(12) United States Patent
Srinivasan

(10) Patent No.: US 12,040,086 B2
(45) Date of Patent: Jul. 16, 2024

(54) PATIENT HEALTH RECORD PORTAL GAMIFICATION

(71) Applicant: MedicalMine, Inc., Pleasanton, CA (US)

(72) Inventor: Pramila Srinivasan, Pleasanton, CA (US)

(73) Assignee: MedicalMine, Inc., Pleasanton, CA (US)

( * ) Notice: Subject to any disclaimer, the term of this patent is extended or adjusted under 35 U.S.C. 154(b) by 480 days.

(21) Appl. No.: 14/838,309

(22) Filed: Aug. 27, 2015

(65) Prior Publication Data

US 2016/0063204 A1 Mar. 3, 2016

Related U.S. Application Data

(60) Provisional application No. 62/042,461, filed on Aug. 27, 2014.

(51) Int. Cl.
*G16H 40/67* (2018.01)
*G16H 10/60* (2018.01)

(52) U.S. Cl.
CPC ............. *G16H 40/67* (2018.01); *G16H 10/60* (2018.01)

(58) Field of Classification Search
CPC .... G06F 19/3418; G16H 40/40; G16H 40/60; G16H 40/67; G16H 10/60
See application file for complete search history.

(56) References Cited

U.S. PATENT DOCUMENTS

| | | | |
|---|---|---|---|
| 11,398,232 B1 | 7/2022 | Agassi et al. | |
| 11,410,650 B1 | 8/2022 | Agassi et al. | |
| 2004/0122736 A1* | 6/2004 | Strock | G06Q 30/0231 |
| | | | 705/14.31 |
| 2011/0184748 A1* | 7/2011 | Fierro | G06Q 10/00 |
| | | | 705/2 |
| 2012/0129139 A1* | 5/2012 | Partovi | G06F 19/3418 |
| | | | 434/262 |
| 2014/0278139 A1* | 9/2014 | Hong | A61B 5/1123 |
| | | | 702/19 |
| 2016/0232329 A1 | 8/2016 | Xu | |
| 2021/0397788 A1 | 12/2021 | Yim | |

* cited by examiner

*Primary Examiner* — Gregory D. Moseley
(74) *Attorney, Agent, or Firm* — Ahmann Kloke LLP

(57) ABSTRACT

Methods and systems for rewarding the usage of specific applications connected to an Electronic Health Record used by healthcare provider offices, such as Patient Portals, to accomplish tasks such as messaging doctors using the inline email-like messaging system for non-urgent matters, for requesting appointments online, for requesting refill requests online, sharing personal health data from tracking devices, etc.

8 Claims, 9 Drawing Sheets

Health Summary

🧴 Medications [Active] [History]

RX

Albuterol 0.09 MG/ACTUAT inhalant solution
2 Puff, Every 6 hours
[InActive]

| ✓ | ✓ | ✓ | ✓ |
|---|---|---|---|
| Morning | Afternoon | Evening | Night |

Metoprolol 25 MG oral tablet
2 Puff, Every 6 hours
[InActive]

| ✓ | | | ✓ |
|---|---|---|---|
| Morning | Afternoon | Evening | Night |

🔬 Labs

Lipid Panel　　　　　　　　　　　　　　　　Dr. Robert Dolin
12:00 PM – Feb. 02, 2013　　　　　　　　　　Good Health Clinic TOTAL CHOLESTROL　　　　　　　　　230
187 mg/dl　　　　　| Low | Normal | High |
Normal　　　　　　　　　　　　　　　201　　240

CBC WO DIFFERENTIAL　　　　　　　　　Dr. Robert Dolin
01:00 PM – Nov. 12, 2012　　　　　　　　　　Good Health Clinic

❤️ Vitals

Nov. 14, 1999

| BMI | Systolic | Diastolic |
|---|---|---|
| 27.45 | 132 mm[Hg] | 86 mm[Hg] |

Show more...

FIG. 8

Rewards   Total points: 460

| Medications Taken | Tracking Lab Records | Immunizations |
| --- | --- | --- |
| ★★☆☆☆ 45 Points | ★★★★☆ 70 Points | ★☆☆☆☆ 25 Points |

| Tracking Vitals | Secured Messages to Providers | Sharing / Receiving Records through Direct |
| --- | --- | --- |
| ★★★★☆ 80 Points | ☆☆☆☆☆ 15 Points | ★★★★☆ 90 Points |

| Electronic Consent | PHR Usage |
| --- | --- |
| ★★☆☆☆ 45 Points | ★★★★★ 95 Points |

Each ★ carries 20 points

[Redeem]

FIG. 9

PATIENT HEALTH RECORD PORTAL GAMIFICATION

CROSS-REFERENCE TO RELATED APPLICATIONS

This application claims the benefit of U.S. Patent Provisional Application No. 62/042,461, filed Aug. 27, 2014, the content of which is hereby incorporated by reference.

BACKGROUND

An area of ongoing research and development is providing health care to patients. In particular research has been conducted in providing health care to patients using electronic health care systems.

Other limitations of the relevant art will become apparent to those of skill in the art upon reading the specification and studying of the drawings.

SUMMARY

The following implementations and aspects thereof are described and illustrated in conjunction with systems, tools, and methods that are meant to be exemplary and illustrative, not necessarily limiting in scope. In various implementations one or more of the above-described problems have been addressed, while other implementations are directed to other improvements.

In various implementations, methods and systems for rewarding the usage of specific applications connected to an Electronic Health Record used by healthcare provider offices, such as Patient Portals, to accomplish tasks such as messaging doctors using the inline email-like messaging system for non-urgent matters, for requesting appointments online, for requesting refill requests online, sharing personal health data from tracking devices, etc.

These and other advantages will become apparent to those skilled in the relevant art upon a reading of the following descriptions and a study of the several examples of the drawings.

BRIEF DESCRIPTION OF THE DRAWINGS

FIG. 8 depicts an example screenshot of an interface of a patient portal through which a user can view their health summary.

FIG. 9 depicts an example screenshot of an interface of a patient portal through which a user can view a rewards summary.

DETAILED DESCRIPTION

Figure 1:
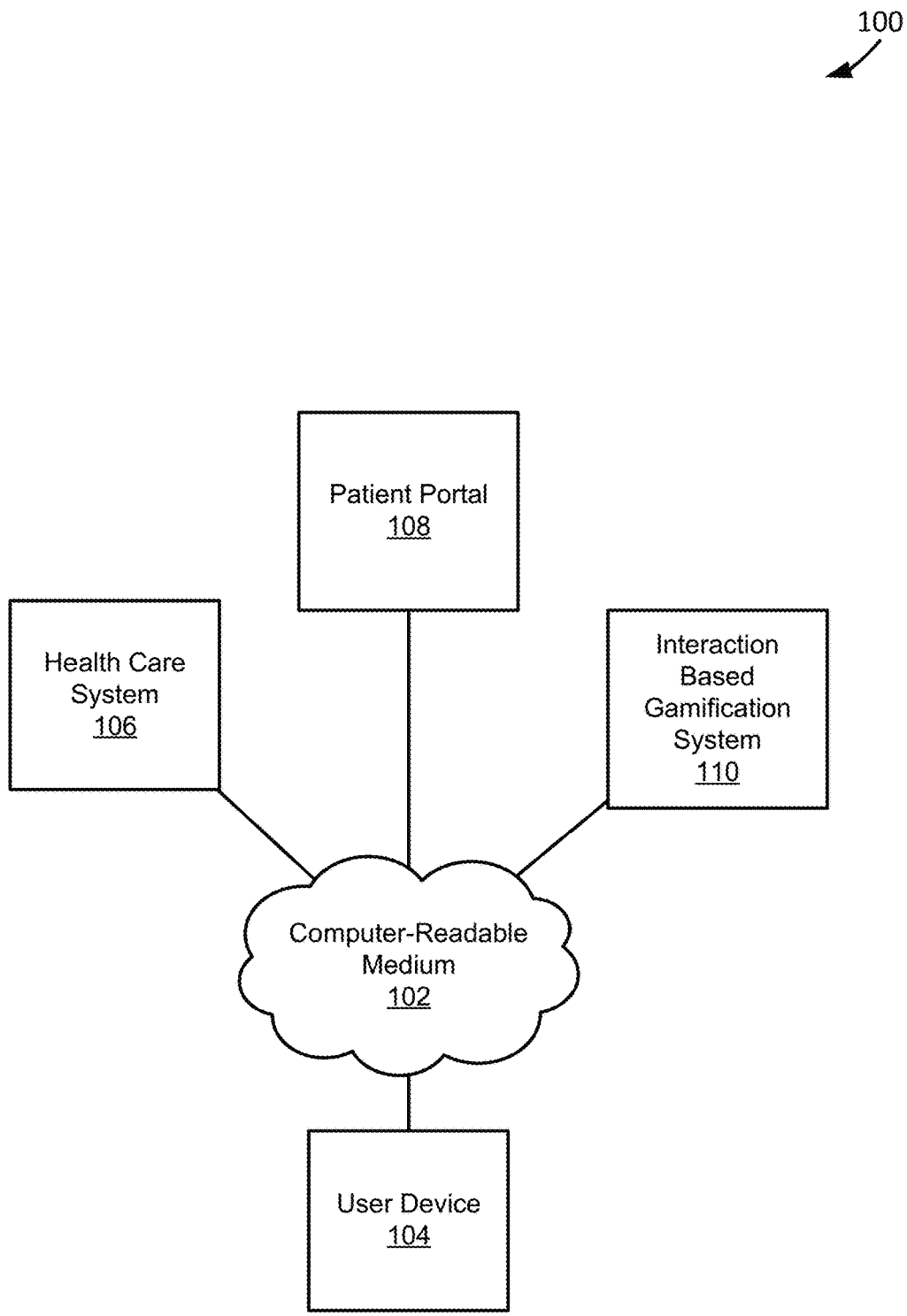
FIG. 1 depicts a diagram of an example of a system for providing gamification of a health care system.

FIG. 1 depicts a diagram 100 of an example of a system for providing gamification of a health care system. The system of the example of FIG. 1 includes a computer-readable medium 102, a user device 104, a health care system, a patient interface 108, and an interaction based gamification system 110.

In the example system shown in FIG. 1, the user device 104, the health care system 106, the patient portal 108, and the interaction based gamification system 110 are coupled to each other through the computer-readable medium 102. As used in this paper, a "computer-readable medium" is intended to include all mediums that are statutory (e.g., in the United States, under 35 U.S.C. 101), and to specifically exclude all mediums that are non-statutory in nature to the extent that the exclusion is necessary for a claim that includes the computer-readable medium to be valid. Known statutory computer-readable mediums include hardware (e.g., registers, random access memory (RAM), non-volatile (NV) storage, to name a few), but may or may not be limited to hardware.

The computer-readable medium 102 is intended to represent a variety of potentially applicable technologies. For example, the computer-readable medium 102 can be used to form a network or part of a network. Where two components are co-located on a device, the computer-readable medium 102 can include a bus or other data conduit or plane. Where a first component is co-located on one device and a second component is located on a different device, the computer-readable medium 102 can include a wireless or wired back-end network or LAN. The computer-readable medium 102 can also encompass a relevant portion of a WAN or other network, if applicable.

The computer-readable medium 102, the user device 104, the health care system 106, the patient portal 108, the interaction based gamification system 110, and other applicable systems or devices described in this paper can be implemented as a computer system, a plurality of computer systems, or parts of a computer system or a plurality of computer systems. In general, a computer system will include a processor, memory, non-volatile storage, and an interface. A typical computer system will usually include at least a processor, memory, and a device (e.g., a bus) coupling the memory to the processor. The processor can be, for example, a general-purpose central processing unit (CPU), such as a microprocessor, or a special-purpose processor, such as a microcontroller.

The memory can include, by way of example but not limitation, random access memory (RAM), such as dynamic RAM (DRAM) and static RAM (SRAM). The memory can be local, remote, or distributed. The bus can also couple the processor to non-volatile storage. The non-volatile storage is often a magnetic floppy or hard disk, a magnetic-optical disk, an optical disk, a read-only memory (ROM), such as a CD-ROM, EPROM, or EEPROM, a magnetic or optical card, or another form of storage for large amounts of data. Some of this data is often written, by a direct memory access process, into memory during execution of software on the computer system. The non-volatile storage can be local, remote, or distributed. The non-volatile storage is optional because systems can be created with all applicable data available in memory.

Software is typically stored in the non-volatile storage. Indeed, for large programs, it may not even be possible to store the entire program in the memory. Nevertheless, it should be understood that for software to run, if necessary, it is moved to a computer-readable location appropriate for processing, and for illustrative purposes, that location is referred to as the memory in this paper. Even when software is moved to the memory for execution, the processor will typically make use of hardware registers to store values associated with the software, and local cache that, ideally, serves to speed up execution. As used herein, a software program is assumed to be stored at an applicable known or convenient location (from non-volatile storage to hardware registers) when the software program is referred to as "implemented in a computer-readable storage medium." A processor is considered to be "configured to execute a program" when at least one value associated with the program is stored in a register readable by the processor.

In one example of operation, a computer system can be controlled by operating system software, which is a software program that includes a file management system, such as a disk operating system. One example of operating system software with associated file management system software is the family of operating systems known as Windows® from Microsoft Corporation of Redmond, Washington, and their associated file management systems. Another example of operating system software with its associated file management system software is the Linux operating system and its associated file management system. The file management system is typically stored in the non-volatile storage and causes the processor to execute the various acts required by the operating system to input and output data and to store data in the memory, including storing files on the non-volatile storage.

The bus can also couple the processor to the interface. The interface can include one or more input and/or output (I/O) devices. The I/O devices can include, by way of example but not limitation, a keyboard, a mouse or other pointing device, disk drives, printers, a scanner, and other I/O devices, including a display device. The display device can include, by way of example but not limitation, a cathode ray tube (CRT), liquid crystal display (LCD), or some other applicable known or convenient display device. The interface can include one or more of a modem or network interface. It will be appreciated that a modem or network interface can be considered to be part of the computer system. The interface can include an analog modem, isdn modem, cable modem, token ring interface, satellite transmission interface (e.g. "direct PC"), or other interfaces for coupling a computer system to other computer systems. Interfaces enable computer systems and other devices to be coupled together in a network.

The computer systems can be compatible with or implemented as part of or through a cloud-based computing system. As used in this paper, a cloud-based computing system is a system that provides virtualized computing resources, software and/or information to client devices. The computing resources, software and/or information can be virtualized by maintaining centralized services and resources that the edge devices can access over a communication interface, such as a network. "Cloud" may be a marketing term and for the purposes of this paper can include any of the networks described herein. The cloud-based computing system can involve a subscription for services or use a utility pricing model. Users can access the protocols of the cloud-based computing system through a web browser or other container application located on their client device.

A computer system can be implemented as an engine, as part of an engine, or through multiple engines. As used in this paper, an engine includes one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors, or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the FIGS. in this paper.

The engines described in this paper, or the engines through which the systems and devices described in this paper can be implemented, can be cloud-based engines. As used in this paper, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

As used in this paper, datastores are intended to include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a general- or specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described in this paper.

Datastores can include data structures. As used in this paper, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described in this paper, can be cloud-based datastores. A cloud-based datastore is a datastore that is compatible with cloud-based computing systems and engines.

The user device 104 functions according to an applicable device through which a user can send and receive data. The user device 104 can be a mobile device. Depending upon implementation-specific or other considerations, the user device 104 can be a thin client or an ultra-thin client. Through the user device 104, a user can interact with a health care system. In interacting with a health care system, a user can send and receive patient data. Patient data includes information related to providing and receiving care and wellness. For example, patient data can include data used in booking appointments, lab results, symptoms, personal information of a patient, contact information of a patient, billing information, intake information, and follow up information. In various implementations, the user device 104 is a kiosk at health care provider location. In such various implementations, a user can login to their account and check in with the health care provider for appointments.

In a specific implementation, the user device 104 functions to transmit patient data captured by a wearable of a user. Wearables include applicable devices for monitoring functioning of a human body. For example, a wearable can be a heart monitor, and readings captured by the heart monitor can be transmitted by the user device 104. In various implementations, the user device 104 includes a wireless interface through it can be wirelessly coupled to wearables. For example the user device 104 can include a Bluetooth® transmitter/receiver which allows it to communicate with wearables as they are worn by a user.

The health care system 106 functions according to an applicable system of a health care provider for providing health care to patients. The health care system 106 can store patient data for a specific patient. Depending upon implementation-specific or other considerations, the health care system 106 can request patient data from a patient. For example, the health care system 106 can request that a user register before treatment is given. In another example, the health care system 106 can request follow up information from a patient after being seen by a health care provider. The health care system 106 can maintain calendars of health care providers. Using calendars of health care providers, the health care system 106 can register appointments for patients.

In a specific implementation, the health care system 106 can send data used by a patient in obtaining medications or outside treatment. In various implementations, the health care system 106 can send an electronic prescription to a pharmacy, where a user can pick up their prescription. Further in the various implementations, the health care system 106 can refill a prescription at a pharmacy using an electronic prescription.

The patient portal 108 functions as a portal through which a user can interact with a health care system. Depending upon implementation-specific or other considerations, the patient portal 108 can be implemented as a native application executing on a user device. Further depending upon implementation-specific or other considerations, the patient portal 108 can be implemented as a web based application that is accessed through a web browser executing at a user device.

In a specific implementation, the patient portal 108 is utilized by a user to schedule appointments with a health care provider. For example, the patient portal 108 can retrieve calendar data of health care providers and provide the calendar data to a user to allow a user to select an available time. Further in the example, the patient portal 108 can transmit data indicating a desired time for a user to a health care provider system, where the user can be scheduled for the desired time.

In a specific implementation, the patient portal 108 is utilized by a user to view patient data. For example, the patient portal 108 can be used to access health records, lab results, medication information, and other applicable information used in providing health care. In various implementations, the patient portal 108 can retrieve patient data from a health care provider system and provide the patient data to a user device.

In a specific implementation, the patient portal 108 is utilized to facilitate communication between a user and health care provider. Specifically, a user can send messages to a health care provider through the patient portal 108. Additionally, a health care provider can send messages to a user through the patient portal 108. Depending upon implementation-specific or other considerations, the patient portal can include a chat window that allows users and health care providers to freely communicate between each other.

In a specific implementation, the patient portal 108 is utilized by a health care provider to manage the providing of health care. Depending upon implementation-specific or other considerations, a health care provider can use the patient portal 108 to access their calendar on a health care system. For example, the patient portal 108 can receive calendar data indicating a schedule of a health care provider and send the calendar data to a user device of the health care provider. Further depending upon implementation-specific or other considerations, a health care provider can use the patient portal 108 to view patient data. For example, a health care provider can user the patient portal 108 to access lab results of one of their patient.

In a specific implementation, the patient portal 108 transmits patient data captured by a wearable device to a health care system. The patient portal 108 can receive patient data captured by a wearable device from a user device or the wearable device itself and subsequently transmit the patient data to a health care system. For example, the patient portal 108 can transmit heart rate readings captured by a heart rate monitor to a health care system. As a result, a health care provider can monitor patients even when they are not at the physical location of the patient.

The interaction based gamification system 110 functions to reward a user for interacting with a health care system through a patient portal. A reward, as used in this paper, includes an applicable incentive for getting a patient to perform at least one task. In various implementations, a reward can be a monetary value or capable of being converted into a monetary value. For example a reward can be points that can be converted to a gift card.

In a specific implementation, the interaction based gamification system can reward a user according to reward rules. Reward rules, as used in this paper, specify a task to complete, an amount of a reward to be given for completing the task, and a reward type to be given for completing a task. For example, a reward rule can specify to give 50 points to a user when they register through a patient portal. Depending upon implementation-specific or other conditions, reward rules can be specific to fitness goals. For example, a reward rule can specify to award 100 points to a user if they walk a mile in a day. Further depending upon implementation-specific or other considerations, reward rules can be specific to health goals. For example, a reward rule can specify to award 100 points to a user if they lose 10 pounds. Depending upon implementation-specific or other considerations, reward rules can be specific to medication goals. For example, a reward rule can specify to award 100 points to a user if they complete a medical regimen.

Reward rules can be generated or specified by an applicable entity for specifying reward rules. In various implementations, a health care provider can specify reward rules.

Depending upon implementation-specific or other considerations, reward rules can be specific to a patient. For example, if a patient needs to lower their blood sugar level, then a health care provider can specify reward rules for tasks related to lowering blood sugar for the patient.

In a specific implementation, the interaction based gamification system 110 can receive data through a patient portal to determine if a user is entitled to a reward. Depending upon implementation-specific or other considerations, the interaction based gamification system 110 can receive patient data captured by a wearable of a user. For example, the interaction based gamification system 110 can receive patient data indicating the amount of steps a user has taken from a pedometer worn by the patient and subsequently determine if the user is entitled to a reward. Further depending upon implementation-specific or other considerations, the interaction based gamification system 110 can receive patient data from a health care system. For example, the interaction based gamification system 110 can receive patient data indicating a user passed a test and subsequently determine if the user is entitled to a reward. Depending upon implementation-specific or other considerations, the interaction based gamification system 110 can receive monitoring data captured by a patient portal itself. Monitoring data includes data indicating how a user interacted with a patient portal and subsequently a health care system through the patient portal. For example the interaction based gamification system 110 can receive monitoring data indicating that a user scheduled an appointment and subsequently determine if the user is entitled to a reward.

In an example of operation of the example system shown in FIG. 1, the user device 104 functions to send data to and receive data from the patient portal 108. In the example of operation of the example system shown in FIG. 1, the patient portal 108 transmits patient data between the health care system 106 and the user device 104. Further, in the example of operation of the example system shown in FIG. 1, the interaction based gamification system 110 rewards a user based on the interactions with the health care system 106 through the patient portal 108 according to rewards rules.

Figure 2:
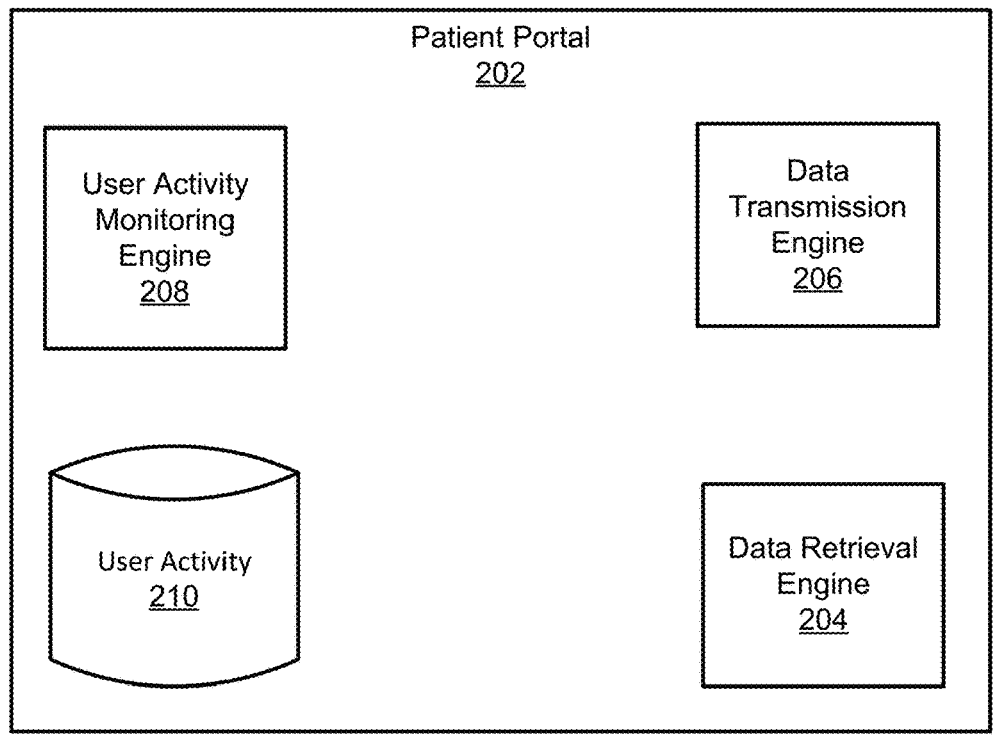
FIG. 2 depicts a diagram of an example of a patient portal.

FIG. 2 depicts a diagram 200 of an example of a patient portal. The example system shown in FIG. 2 includes a patient portal 202. The patient portal 202 functions according to an applicable system for transmitting data between a user device and a health care system, such as the patient portals described in this paper. The patient portal 202 can retrieve patient data from either or both a health care system and a user device and subsequently transmit the patient data. The patient portal 202 can transmit patient data to either or both a health care system and a user device.

The patient portal 202 shown in FIG. 2 includes a data retrieval engine 204, a data transmission engine 206, a user activity monitoring engine 208, and a user activity datastore 210. The data retrieval engine 204 functions to retrieve data from either or both a user device and a health care system. The data retrieval engine 204 can retrieve patient data. For example, the data retrieval engine 204 can retrieve test results from a health care system. Depending upon implementation-specific or other considerations, the data retrieval engine 204 can retrieve patient data captured by a wearable device of a user from a user device. For example, the data retrieval engine 204 can capture data indicating a heart rate of a patient.

In a specific implementation, the data retrieval engine 204 can request data and subsequently retrieve the requested data. Depending upon implementation-specific or other considerations, the data retrieval engine 204 can request data from a user. For example, the data retrieval engine 204 can request that a user provide their demographic information for registering the user to access patient data through the patient portal 202. In another example, if a user inputs that they want to access their test results, then the data retrieval engine 204 can request the test results from a health care system.

The data transmission engine 206 functions to transmit data to either or both a user device and a health care system. The data transmission engine 206 can transmit patient data. For example, the data transmission engine 206 can transmit test results to a user device. Depending upon implementation-specific or other considerations, the data transmission engine 206 can transmit patient data captured by a wearable device of a user from a user device. For example, the data transmission engine 206 can transmit data indicating a heart rate of a patient to a health care system.

In a specific implementation, the data transmission engine 206 functions to transmit data indicating activities that are eligible for reward as the user interacts with the patient portal 202. In various implementations, reward eligible activities are marked by indicia that can be activated to indicate what reward is available. For example, the data transmission engine 206 can provide an email form with a ribbon indicating that sending of an email to a health care provider earns a user 5 points.

The user activity monitoring engine 208 functions to track activity of a user. In tracking activity of a user, the user activity monitoring engine 208 can monitor how a user interacts with the patient portal 202, and subsequently a health care system through the patient portal 202. Depending upon implementation-specific or other considerations, the user activity monitoring engine 208 can determining activities performed by a user based on data transmitted through the patient portal 202. For example if lab results are sent to a user device, then the user activity monitoring engine 208 can determine that a user has viewed their lab results.

The user activity datastore 210 functions to store monitoring data. Monitoring data stored in the user activity datastore 210 can be generated by the user activity monitoring engine 208. For example, if a user makes an appointment to visit a health care provider, then the user activity datastore 210 can store monitoring data indicating that the user made an appointment to visit a health care provider.

In an example of operation of the example system shown in FIG. 2, the data retrieval engine 204 retrieves patient data from a user device. In the example of operation of the example system shown in FIG. 2, the data transmission engine 206 transmits the patient data to a health care system. Further, in the example of operation of the example system shown in FIG. 2, the user activity monitoring engine 208 generate monitoring data stored in the user activity datastore 210 based on the patient data.

Figure 3:
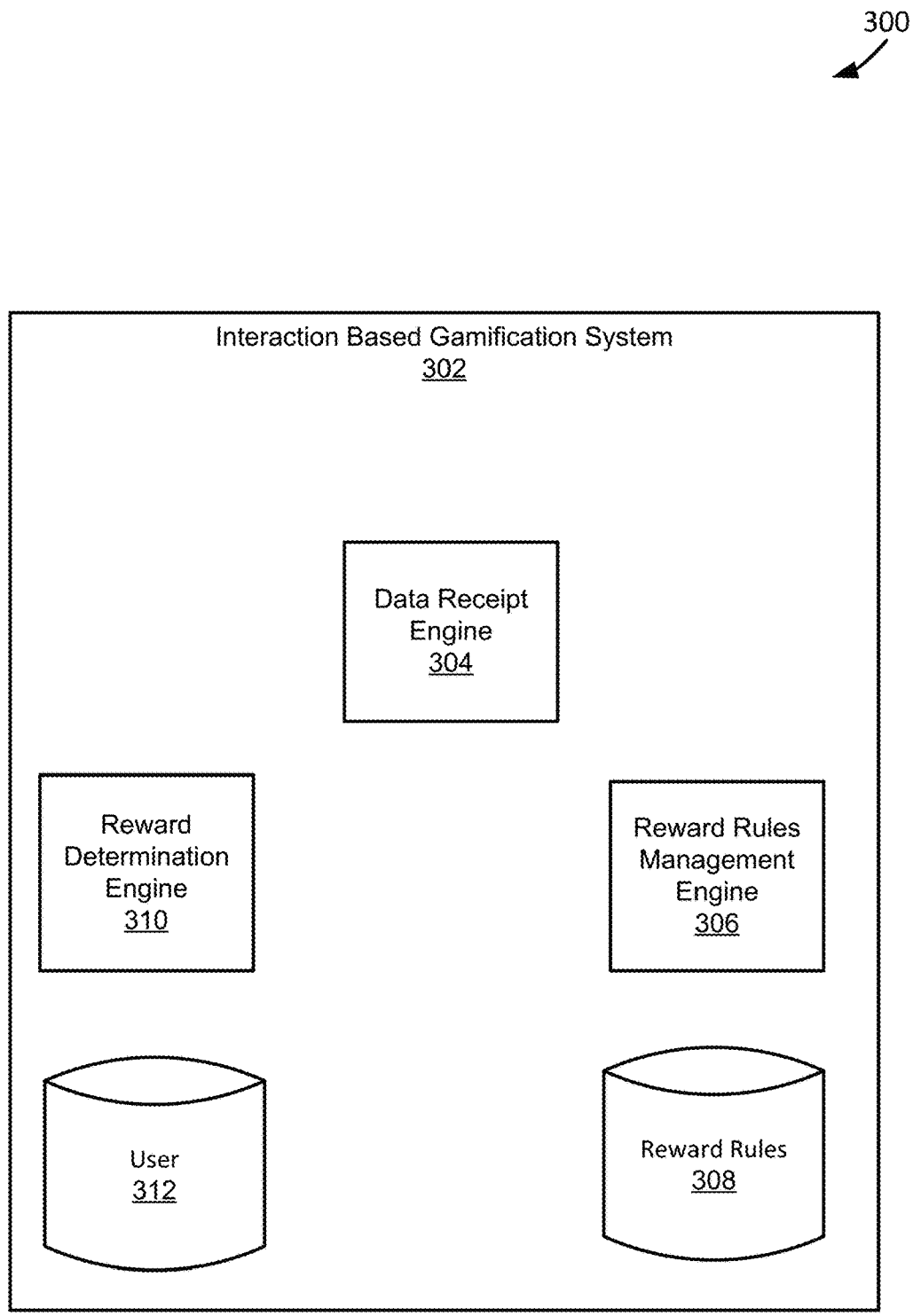
FIG. 3 depicts a diagram of an interaction based gamification system for a patient portal.

FIG. 3 depicts a diagram 300 of an interaction based gamification system for a patient portal. The example system shown in FIG. 2 includes an interaction based gamification system 302. The interaction based gamification system 302 functions according to an applicable system for providing rewards to users based on their interactions with a patient portal, such as the interaction based gamification systems described in this paper. The interaction based gamification system 302 can provide rewards based on monitoring data or patient data collected for a user. For example, if patient data indicates a user has lost 10 pounds, then the interaction based gamification system 302 can provide a reward to the user.

The interaction based gamification system 302 shown in FIG. 3 includes a data receipt engine 304, a reward rules management engine 306, a reward rules datastore 308, a reward determination engine 310, and a user datastore 312. The data receipt engine 304 functions to receive data used in determining whether to provide a reward to a user. Depending upon implementation-specific or other considerations, the data receipt engine 304 can receive patient data from either or both a health care system or a user device through a patient portal. For example, the data receipt engine 304 can receive test results for a patient. In another example the data receipt engine 304 can receive patient data captured by a wearable utilized by a user. Further depending upon implementation-specific or other considerations, the data receipt engine 310 receives monitoring data from a patient portal. For example, the data receipt engine 304 can receive monitoring data indicating that a user has scheduled an appointment with a health care provider.

The reward rules management engine 306 functions to manage reward rules. In managing reward rules, the reward rules management engine 306 can generate and/or update reward rules data indicating reward rules. In managing reward rules, the reward rules management engine 306 can determine a task to reward, a type of reward to give for completing the task, and an amount of reward to give. The reward rules management engine 306 can manage reward rules according to received input. For example, a health care provider can input tasks to reward, a type of reward to give, and an amount of reward to give, and the reward rules management engine 306 can subsequently create reward rules according to the input.

In a specific implementation, the reward rules management engine 306 manages reward rules specific to a user. In managing reward rules specific to a user, the reward rules management engine 306 can create reward rules to apply to a specific user. The reward rules management engine 306 can generate reward rules data indicating the reward rules and an identifier of a user specific to the reward rules.

The reward rules datastore 308 functions to store reward rules data indicating reward rules. Reward rules data stored in the reward rules datastore 308 can indicate a task to provide an award for, a type of reward to provide, and an amount of reward to provide.

The reward determination engine 310 functions to determine whether to give a reward to a user. The reward determination engine 310 can determine whether to give a reward to a user according to receive data. Depending upon implementation-specific or other considerations, the reward determination engine 310 can determine whether to give a reward to a user based on receiving monitoring data. For example, the reward determination engine 310 can determine that a user has scheduled an appointment based on monitoring data, and subsequently give a reward to the user. Further depending upon implementation-specific or other considerations, the reward determination engine 310 can determine whether to give a reward to a user based on received patient data for the user. For example, the reward determination engine 310 can determine that a user has passed a health screening, and subsequently give a reward to the user. In another example, the reward determination engine 310 can determine that a user has walked a mile in a day, based on patient data captured from a wearable, and subsequently give a reward to the user.

The reward determination engine 310 determines whether to give a reward to a user according to reward rules. In using reward rules to determine whether to give a reward, the reward determination engine 310 can determine a task to give an award for upon completion. For example, the reward determination engine 310 can determine to provide a reward when a patient successfully registers to use a patient portal. Further, in using reward rules to determine whether to give a reward, the reward determination engine 310 can determine a reward type to give. For example, the reward determination engine 310 can determine to reward a user with points. Additionally, in using reward rules to determine whether to give a reward, the reward determination engine 310 can determine an amount to reward a user. For example, the reward determination engine 310 can determine to reward a user 50 points.

In a specific implementation, the reward determination engine 310 notifies a user that they have received a reward. The reward determination engine 310 can notify a user that they have received a reward through a patient portal. For example the reward determination engine 310 can send a message to a user device of a user through a patient portal indicating that they have been rewarded. In various implementations, the reward determination engine 310 notifies a user an activity the user has completed to receive a reward, a type of reward the user has received, and/or an amount of reward the user has received.

In a specific implementation, the reward determination engine 310 provides a summary of earned rewards to a user. A summary of earned rewards can include an indication of rewards earned for different subsets of activities. For example, a summary of earned rewards can include that a user earned 70 points by tracking their lab activities and 45 points by taking their medication properly.

The user datastore 312 functions to store user reward data. User reward data specifies rewards a user has received, activities the user completed to receive a reward, types of rewards the user has received, and the amounts of each reward the user has received.

In an example of operation of the example system shown in FIG. 3, the data receipt engine 304 receives data from a patient portal. In the example of operation of the example system shown in FIG. 3, the reward rules management engine 306 manages reward rules indicated by reward rules data stored in the reward rules datastore 308. Further, in the example of operation of the example system shown in FIG. 3, the reward determination engine 310 determines whether to grant a user a reward based on the reward rules indicated by the reward rules data stored in the reward rules datastore 308 and the data received from the patient portal by the data receipt engine 304. In the example of operation of the example system shown in FIG. 3, the user datastore 312 stores user reward data generated by the reward determination engine 310 and indicating reward a user has been granted.

Figure 4:
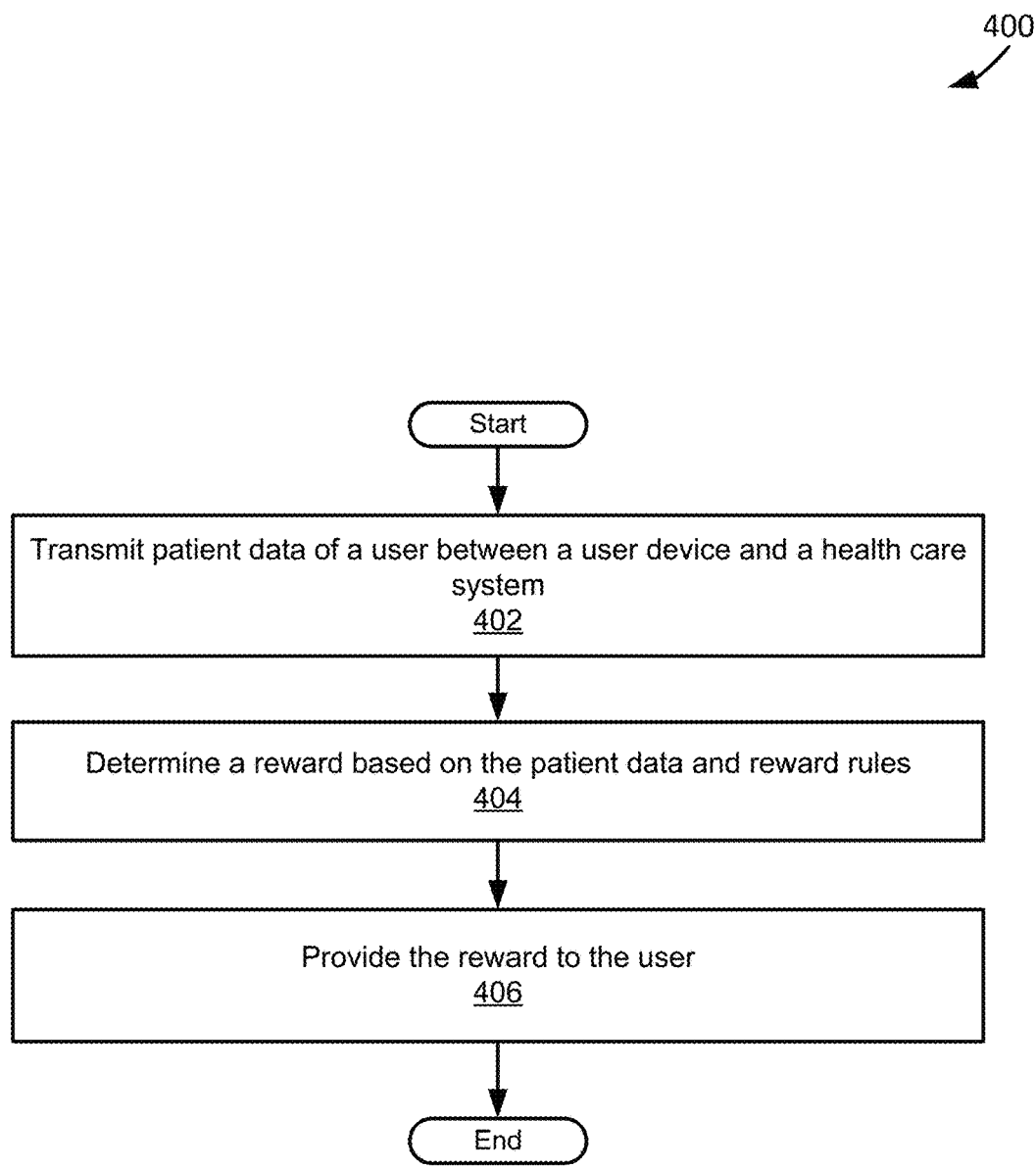
FIG. 4 depicts a flowchart of an example of a method for rewarding a user for interacting with a health care system through a patient portal.

FIG. 4 depicts a flowchart 400 of an example of a method for rewarding a user for interacting with a health care system through a patient portal. The flowchart 400 begins at module 402, where patient data of a user is transmitted between a user device and a health care system through a patient portal. An applicable system for transmitting patient data between a user device and a health care system, such as the patient portals described in this paper, can transmit the patient data between a user device and health care system. In a specific implementation, patient data of a user is data captured by a wearable of the user. For example, patient data can include data indicating that a user has walked a mile in a day.

The flowchart 400 continues to module 404, where a reward is determined based on the patient data and reward rules. An applicable system for determining a reward, such as the reward determination engines described in this paper, can determine a reward based on the patient data and reward rules. In determining a reward, a task that has been completed or an accomplishment that has been achieved can be determined from the patient data. The task or accomplishment can then be looked up in the reward rules to determine whether to give a reward, a reward type to give, and a reward amount to give.

The flowchart 400 continues to module 406, where the reward is provided to the user. In various implementations, the reward can be claimed by the user through a patient portal. Further in various implementations, a notification can be sent to the user indicating that the user has been give the reward. The notification can be sent as part of a reward summary indicating all of the rewards that have been given to the user.

Figure 5:
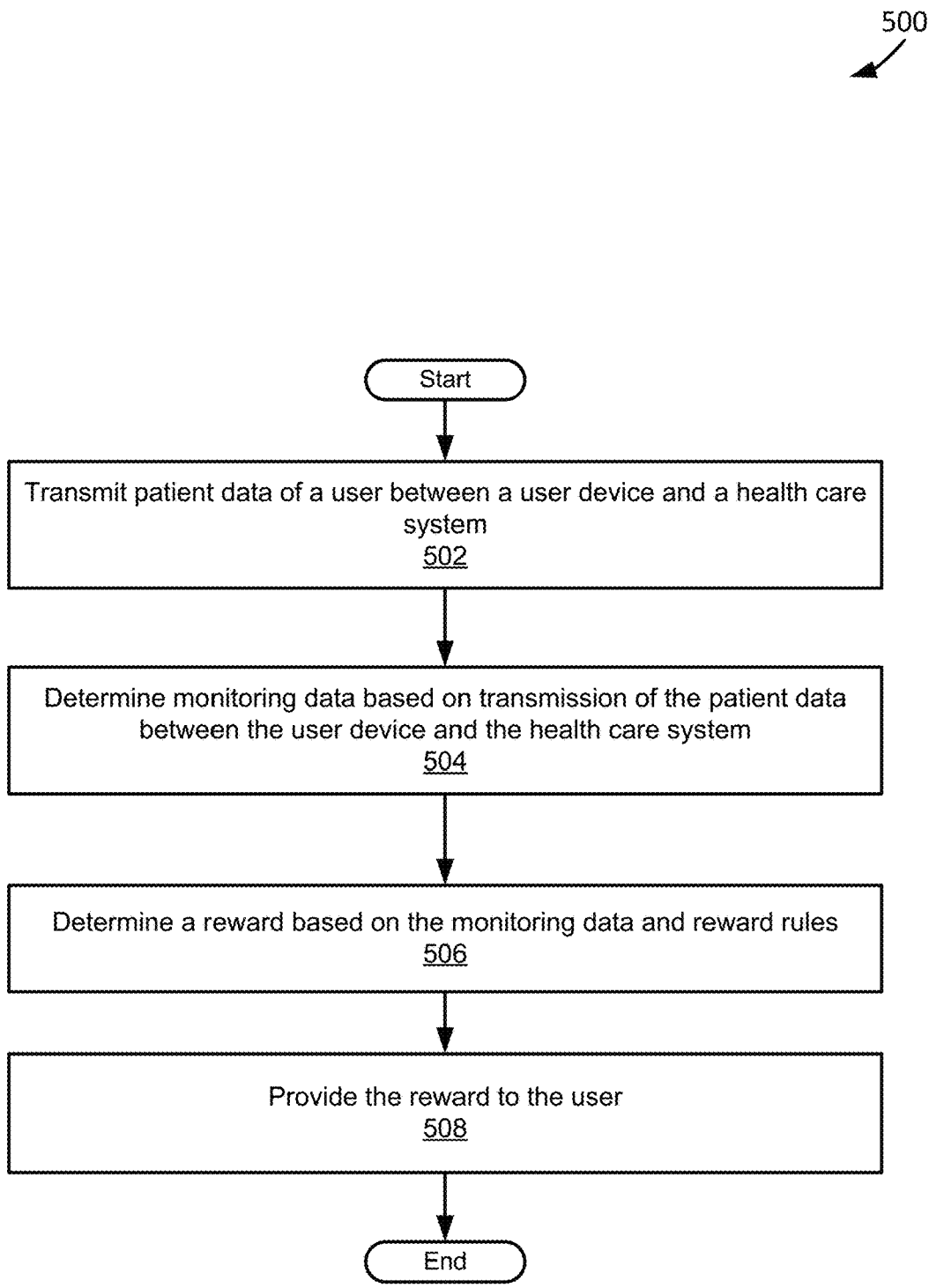
FIG. 5 depicts a flowchart of an example of a method for rewarding a user for interacting with a health care system through a patient portal.

FIG. 5 depicts a flowchart 500 of an example of a method for rewarding a user for interacting with a health care system through a patient portal. The flowchart 500 begins at module 502, where patient data of a user is transmitted between a user device and a health care system through a patient portal. An applicable system for transmitting patient data between a user device and a health care system, such as the patient portals described in this paper, can transmit the patient data between a user device and health care system. In a specific implementation, patient data of a user is data captured by a wearable of the user. For example, patient data can include data indicating that a user has walked a mile in a day.

The flowchart 500 continues to module 504, where monitoring data is determined based on the transmission of the patient data between the user device and the health care system. An applicable system for determining monitoring data, such as the user activity monitoring engines described in this paper, can determine monitoring data based on the transmission of the patient data between the user device and the health care system. Monitoring data can be determined based on what type of patient data is transmitted between the user device and the health care system. For example, if a test result is transferred from the health care system to the user device, then monitoring data can indicate that a user is viewing their test results.

The flowchart 500 continues to module 506, where a reward is determined based on the monitoring data and reward rules. An applicable system for determining a reward, such as the reward determination engines described in this paper, can determine a reward based on the patient data and reward rules. In determining a reward, a task that has been completed or an accomplishment that has been achieved can be determined from the patient data. The task or accomplishment can then be looked up in the reward rules to determine whether to give a reward, a reward type to give, and a reward amount to give.

The flowchart 500 continues to module 508, where the reward is provided to the user. In various implementations, the reward can be claimed by the user through a patient portal. Further in various implementations, a notification can be sent to the user indicating that the user has been give the reward. The notification can be sent as part of a reward summary indicating all of the rewards that have been given to the user.

Figure 6:
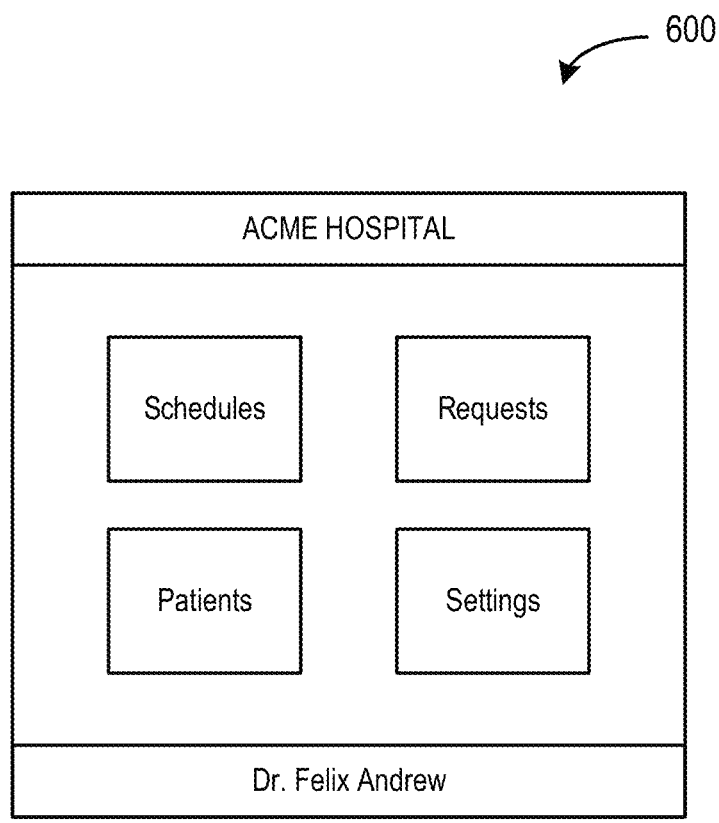
FIG. 6 depicts an example screenshot of an interface of a patient portal through which a health care provider can manage healthcare.

FIG. 6 depicts an example screenshot 600 of an interface of a patient portal through which a health care provider can manage healthcare. The interface includes a schedule tab that can be activated to view a schedule for health care provider. The interface also includes a patients tab through which a health care provider can with patient data. Additionally, the interface includes a requests tab through which a health care provider can view requests and act accordingly.

Figure 7:
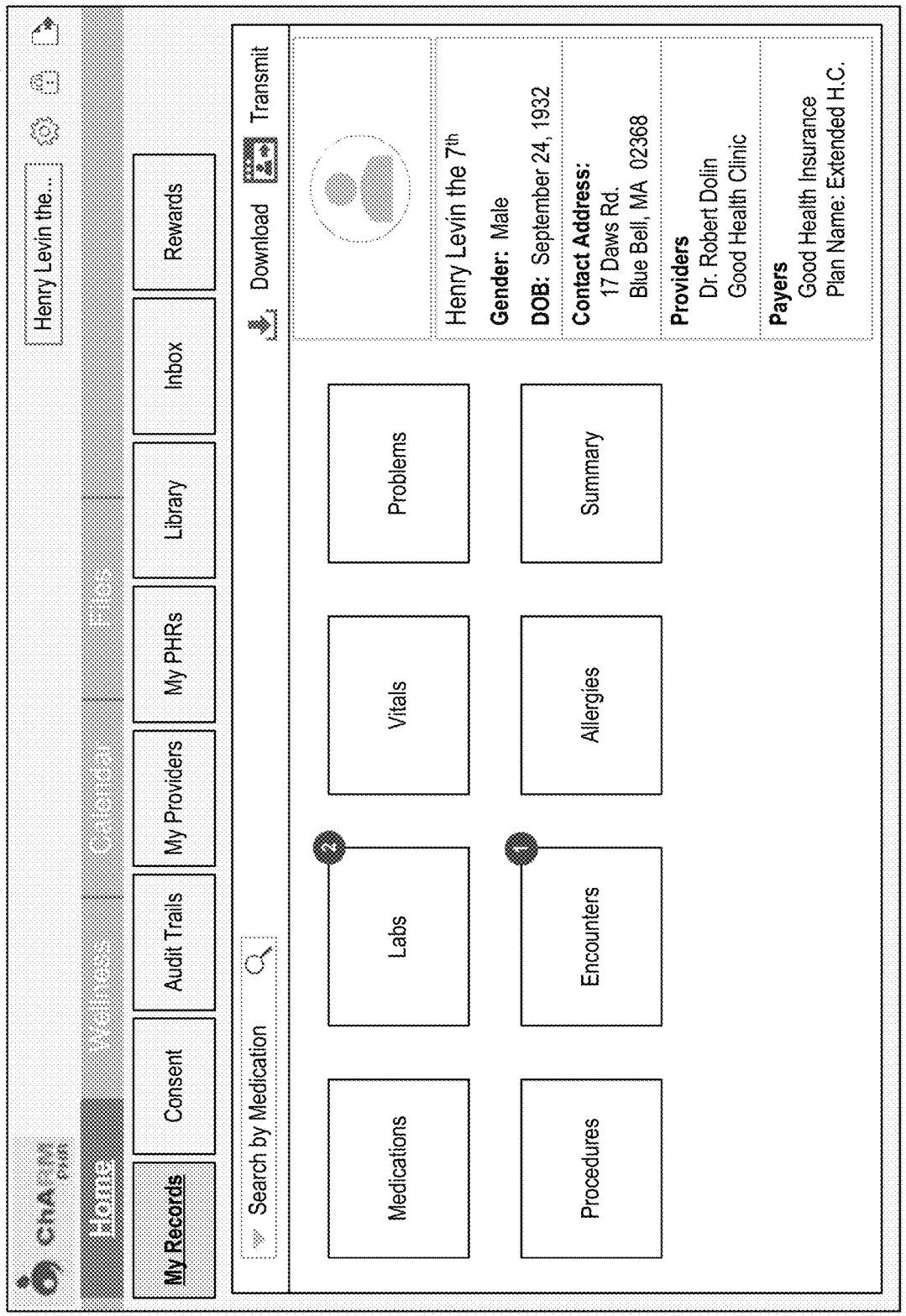
FIG. 7 depicts an example screenshot of an interface of a patient portal through which a user can view patient data.

FIG. 7 depicts an example screenshot 700 of an interface of a patient portal through which a user can view patient data. The interface includes a medications tab through which a user can view medication information, including information related to medications given the user. The interface also includes a labs tab through which a user can monitor their lab and test results. Additionally, the interface includes a vitals tab through which a user can monitor their vital statistics. Further, the interface includes a procedures tab through which a user can view information related to procedures, including procedures that have been or will be performed on the user. The interface also includes an encounters tab, through which a user can view appointments a user has or appointments to which a user has attended.

FIG. 8 depicts an example screenshot 800 of an interface of a patient portal through which a user can view their health summary. The interface includes ribbons. The ribbons can be activated to reveal a reward a user can receive based on completing tasks. For example, the vitals section includes a ribbon that can be activated to indicate rewards a user can receive based on their vitals.

FIG. 9 depicts an example screenshot 900 of an interface of a patient portal through which a user can view a rewards summary. The interface includes a medication section indicating the rewards a user has earned for their medication taking. The interface also includes a section for tracking lab records indicating the rewards a user has earned for tracking their lab results. Additionally, the interface includes an immunization section indicating the rewards a user has earned for their immunizations. Further, the interface includes a vitals section indicating the rewards a user has earned for tracking their vitals. The interface also includes a message section indicating the rewards a user has earned in sending messages to providers. The interface includes a sharing records section indicating the rewards a user has earned for receiving their health records. The interface also includes a consent section indicating rewards a user has earned in providing electronic consent. Additionally, the interface includes a PHR usage section indicating the rewards a user has earned in using a patient portal. The interface includes a redemption button that upon activation causes a user to redeem their rewards.

These and other examples provided in this paper are intended to illustrate but not necessarily to limit the described implementation. As used herein, the term "implementation" means an implementation that serves to illustrate by way of example but not limitation. The techniques described in the preceding text and figures can be mixed and matched as circumstances demand to produce alternative implementations.

I claim:

1. A system comprising:

An electronic healthcare kiosk, wherein the electronic healthcare kiosk is positioned at a location of a healthcare provider;

a wearable monitoring device of a user configured to be continuously worn by the user and to capture first patient data of the user, the first patient data comprising data that is inputted by the user via an application on the electronic healthcare kiosk and data that is captured by the wearable monitoring device that is worn by the user and is in wireless communication with the electronic healthcare kiosk, the first patient data including heart monitor readings and a distance the user has walked or run in a period of time, the wearable monitoring device being distinct from the electronic healthcare kiosk a patient portal comprising:
- a data retrieval engine configured to receive, from the electronic healthcare kiosk over a network, the first patient data of the user;
- a data transmission engine configured to transmit second patient data of the user from a health care system to the electronic healthcare kiosk over the network as the user interacts with the patient portal, thereby enabling the electronic healthcare kiosk to present the second patient data to the user, the second patient data comprising health records, lab results including lab results for a blood sugar level of the user, test results, vital statistics, procedure information, and medication information;
- a user activity monitoring engine configured to capture interaction data of the user, the interaction data indicating at least one user interaction with the health care system using the patient portal, the at least one user interaction with the health care system using the patient portal including the user viewing the lab results for the blood sugar level of the user; and
- an interface configured to indicate rewards provided to the user and enable redemption of the rewards by the user, wherein the interface is further configured to present, based on the second patient data of the user, a plurality of activities marked by a respective graphical ribbon indicating an eligibility for at least one reward, wherein activation of a particular respective graphical ribbon reveals on the interface a respective reward value associated with a particular activity of the plurality of activities presented on the interface, wherein the plurality of activities presented on the interface include health record activities associated with the health records of the second patient data, lab result activities associated with the lab results of the second patient data, test result activities associated with the test results of the second patient data, vital statistics activities associated with the vital statistics of the second patient data, procedure information activities associated with the procedure information of the second patient data, and medication information activities associated with the medication information of the second patient data; and an interaction based gamification system comprising:
- a data receipt engine configured to obtain the first patient data, the second patient data, and the interaction data of the user from the patient portal;
- a reward rules management engine configured to generate one or more reward rules specified by the healthcare provider of the user, the one or more reward rules being different from the rewards, the one or more reward rules being specific to the user based on a health condition of the user and being associated with a task to complete or a goal to attain of lowering the blood sugar level of the user, a reward type, and a reward amount, wherein the one or more reward rules are specified by the healthcare provider of the user in order to lower the blood sugar level of the user based on the health condition of the user; and
- a reward determination engine configured to:
  - determine if the user has completed the task or attained the goal of lowering the blood sugar level of the user by comparing the lab results for the blood sugar level of the user to previous lab results for the blood sugar level of the user;
  - if the user has completed the task or attained the goal of lowering the blood sugar level of the user, determine a particular reward by applying the one or more reward rules to the first patient data, the second patient data, and the interaction data;
  - provide, in response to a determination of the particular reward, the particular reward to the user through the patient portal;
  - provide a summary of earned rewards to the user, the summary indicating a first portion of the earned rewards that are associated with the first patient data, a second portion of the earned rewards that are associated with viewing of a first portion of the second patient data by the user, a third portion of the earned rewards that are associated with viewing of a second portion of the second patient data by the user, and a fourth portion of the earned rewards that are associated with the interaction data, wherein the summary of earned rewards includes a summary of the particular reward and a plurality of other rewards;
  - in response to the determination of the particular reward, activate a link in the patient portal that enables the user to redeem the particular reward; and
  - send a notification to the user indicating that the particular reward has been provided to the user, the notification including the summary of earned rewards.

2. The system of claim 1, wherein the interaction data further indicates a user interaction to access specific patient data through the patient portal.

3. The system of claim 1, wherein the interaction data further indicates a user interaction to update specific patient data through the patient portal.

4. The system of claim 1, wherein the interaction data further indicates a user interaction to perform a specific communication with the health care system through the patient portal.

5. The system of claim 1, wherein the particular reward includes a first reward value associated with the first patient data, a second reward value associated with the second patient data, and a third reward value associated with the interaction data.

6. The system of claim 1, wherein the patient portal is further configured to present information on the particular reward on a user interface thereof, the user interface including a first object indicating a first reward value associated with the first patient data, a second object indicating a second reward value associated with the second patient data, and a third object indicating a third reward value associated with the interaction data.

7. The system of claim 1, wherein the reward determination engine determines the particular reward by determining whether to provide a reward, and determining a reward amount responsive to determining to provide a reward.

8. The system of claim 1, wherein the reward rules management engine is configured to update the one or more reward rules based on an input from the health care system.

* * * * *